United States Patent [19]

Melnik et al.

[11] Patent Number: 5,591,446
[45] Date of Patent: Jan. 7, 1997

[54] METHODS AND AGENTS FOR THE PROPHYLAXIS OF ATOPY

[75] Inventors: Bodo C. Melnik, Gütersloh; Gerd Plewig, München, both of Germany

[73] Assignee: Beiersdorf, A.G., Hamburg, Germany

[21] Appl. No.: 420,334

[22] Filed: Apr. 11, 1995

Related U.S. Application Data

[63] Continuation of Ser. No. 7,171, Jan. 21, 1993, abandoned, which is a continuation-in-part of Ser. No. 503,821, Apr. 3, 1990, abandoned.

[30] Foreign Application Priority Data

| Apr. 4, 1989 | [DE] | Germany | 39 10 761.2 |
| Apr. 4, 1989 | [DE] | Germany | 39 10 760.4 |
| Sep. 14, 1989 | [DE] | Germany | 39 30 816.2 |

[51] Int. Cl.$^6$ .................................................. A61K 31/20
[52] U.S. Cl. ...................... 424/439; 426/648; 426/801; 514/558; 514/560
[58] Field of Search ........................ 424/439, 450, 424/400; 514/885, 558, 559, 560; 426/801, 104, 585, 648, 656, 654

[56] References Cited

U.S. PATENT DOCUMENTS

| 2,611,706 | 9/1952 | Bernhart et al. | 99/118 |
| 4,009,282 | 2/1977 | Voorhees | 424/317 |
| 4,477,432 | 10/1984 | Hardie | 424/85 |
| 4,499,085 | 2/1985 | Masuda | 514/58 |
| 4,670,285 | 6/1987 | Clandinin et al. | 426/602 |
| 4,681,896 | 7/1987 | Horrobin | 514/552 |
| 4,703,060 | 10/1987 | Traitler et al. | 514/549 |
| 4,703,069 | 10/1987 | Brown et al. | 521/174 |
| 4,721,626 | 1/1988 | Rule | 426/601 |
| 4,753,926 | 6/1988 | Lucas et al. | 514/2 |
| 4,868,212 | 9/1989 | Horrobin | 514/552 |
| 4,938,984 | 7/1990 | Traitler et al. | 426/580 |
| 4,950,656 | 8/1990 | Lichtenberger | 514/78 |
| 4,963,384 | 10/1990 | Heine et al. | 426/580 |
| 5,000,975 | 3/1991 | Tomarelli | 426/602 |
| 5,013,569 | 5/1991 | Rubin | 426/585 |
| 5,082,664 | 1/1992 | Lenk et al. | 424/450 |

FOREIGN PATENT DOCUMENTS

| 0100630 | 2/1984 | European Pat. Off. | C07C 177/00 |
| 0252716 | 1/1988 | European Pat. Off. | C12P 7/64 |
| 0257859 | 3/1988 | European Pat. Off. | A61K 37/54 |
| 0292403 | 11/1988 | European Pat. Off. | A61K 9/50 |
| 3315356 | 11/1983 | Germany | A61K 31/557 |
| 3403251 | 8/1984 | Germany | A61K 31/20 |
| 62-223120 | 10/1987 | Japan | A61K 31/557 |
| 63-116643 | 5/1988 | Japan | A23D 5/00 |
| 63-145230 | 6/1988 | Japan | A61K 31/557 |

OTHER PUBLICATIONS

Strannegard et al. Int. Archs. Allergy appl. Immun. 82, 422 (1987).
Bjorkstein Acta Pediatr. Scand. Suppl. 351, 76, 1989.
Manku et al. Prostaglandins, Leukotrienes Med. 9, 615, 1982.
U. M. Sarrinen et al., *The Lancet*, pp. 163–166, 28 Jul. 1979.
R. E. Midwinter et al., *The Lancet*, p. 339, 6 Feb. 1982.
S. Wright and J. L. Burton, *The Lancet*, pp. 1120–1122 (1982).
N.–I. M. Kjellman, *Allergy*, vol. 37, pp. 463–473 (1982).
M. S. Manku et al., *British Journal of Dermatology*, vol. 110, pp. 643–648, (1984).
*Chemical Abstracts*, vol. 98, No. 69996v (1983).
*Chemical Abstracts*, vol. 100, No. 80453w, (1984).
Mayer, et al., *Chem. & Phys. of Lipids*, vol. 40, pp. 333–345 (1986).
Rocklin, et al., *Lipids*, vol. 21 pp. 17–20 (1986).
R. S. Zeiger, et al., "*Journal of Allergy and Clinical Immunology*", vol. 78, pp. 224–238 (Jul. 1986).
R. E. Rocklin and L. Thistle, *Cellular Immunology*, vol. 99, pp. 294–299 (1986).
Bordoni, et al., *Drugs Exptl. Clin. Res.*, vol. XIV, pp. 291–297 (1987).
*Chemical Abstracts*, vol. 109, No. 127829b (1988).
*Chemical Abstracts*, vol. 109, No. 209935x, (Jul. 1988).
J. Pene et al., *Proc. Natl. Acad. Sci., USA*, vol. 85, pp. 6880–6884, (Sep. 1988).
P. L. Biagi et al., *Drugs Expt. Clin. Res.*, vol. XIV, pp. 285–290 (1988).
P. M. Shipman et al., *Journal of Immunology*, vol. 140, pp. 2714–2720 (Apr. 1989).
B. C. Melnik and G. Plewig, *Journal of the American Academy of Dermatology*, vol. 21, pp. 557–563 (Sep. 1989).
J. Pene et al., *Journal of Cellular Biochemistry*, vol. 39, pp. 253–264 (1989).
S. Wright and C. Bolton, *British Journal of Nutrition*, vol. 62, pp. 693–697 (1989).
D. F. Horrobin and M. S. Manku in *Omega-6 Essential Fatty Acids*, D. F. Horrobin, ed., (Wiley–Liss 1990), pp. 21–53.
N.–I. M. Kjellman et al., *Allergy Proceedings*, vol. 12, pp. 245–249 (Jul./Aug. 1991).

(List continued on next page.)

*Primary Examiner*—Gollamudi S. Kishore
*Attorney, Agent, or Firm*—Lieberman & Nowak, LLP

[57] ABSTRACT

A method for atopy prophylaxis involves administering an agent comprising γ-linolenic acid, dihomo-γ-linolinic acid, the physiologically compatible salts, esters, amides, phospholipids, glycolipids thereof, and/or prostaglandin $E_1$ ($PGE_1$), $PGE_1$ derivatives, $PGE_1$ analogs to preimmunocompetent humans to prevent the occurrence of atopy. These agents are typically contained in a baby food or are supplied to the baby concurrently. These foods may contain one or more thymus hormones. The use of $PGE_1$, its derivatives and analogs and the physiologically compatible esters, amides, phospholipids and glycolipids thereof in a pharmacologically effective dosage form for the topical or inhalative treatment of acute manifest atopy in the dermal and mucosal areas. These substances are preferably used in combination with γ-linolinic acid, and dihomo-γ-linolinic acid, and/or the physiologically compatible salts, esters, amides, phospholipids and glycolipids thereof.

14 Claims, No Drawings

OTHER PUBLICATIONS

P. G. Holt et al., *Clinical and Experimental Allergy*, vol. 22, pp. 1093–1099 (1992).

B. Dvorak and R. Stepankova, *Prostaglandins Leukotrienes and Essential Fatty Acids*, vol. 46, pp. 183–190 (1992).

B. Melnik and G. Plewig, *Acta Derm Venerol (Stockh)*, Suppl. 176, pp. 77–85 (1992).

A. Berger et al., *Journal of Nutrition*, vol. 123, pp. 225–233 (1993).

*Roche Lexicon Medzin*, (Urban & Schwarzenberg, Baltimore) pp. 1290, 1297.

METHODS AND AGENTS FOR THE PROPHYLAXIS OF ATOPY

This application is a continuation of application Ser. No. 08/007,171, filed 21 Jan. 1993, now abandoned, which in turn is a continuation-in-part of application Ser. No. 09/503,821, filed 3 Apr. 1990, now abandoned, the contents of which are incorporated herein by reference.

BACKGROUND OF THE INVENTION

The subject invention relates to a method for atopy prophylaxis, agents for use therein and methods for preparing and using same.

Atopy is generally understood to mean a familially occurring hypersensitivity to environmental substances of skin and mucosae, with an increased predisposition to develop immediate hypersensitivity to substances originating from the natural environment. It has been postulated that environmental substances induce the production of antibodies of class IgE (immunoglobulin E), which initiate further allergic reactions. Atopy is manifest at the loci of contact with the so-called "allergens" (environment-derived substances such as pollen, spores, domestic dust, etc.), for example in the eyes as an allergic conjunctivitis;

at the nasal mucosa as an allergic rhinitis (hay fever);

in the lungs as an allergic bronchial asthma;

on the skin as chronic or chronic-relapsing dermatitis (atopic dermatitis).

Atopy appears to be genetically-linked and afflicts about 10% of the population, with a recent increase in occurrence. Although medical science has long desired a prophylaxis of atopy and an enhancement of the quality of life, the recent increase in frequency has now exacerbated this need.

By the 1920s, it was recognized that early childhood nutrition plays an important role in preventive medicine. R. S. Zeiger et al., in "*Journal of Allergy and Clinical Immunology*", 78 (1 Part 2):224–238 (1986), stated that breast-feeding in combination with a delayed supply of solid nutrients is suitable to alleviate atopic dermatitis and food allergies in early childhood. Moreover, similar results were obtained by U. M. Saarinen, et al. (in "The Lancet", Jul. 28, 1979, pp. 163–166), where the authors of this clinical study attempted to explain the effect of prolonged breast-feeding in terms immunoglobulin A (IgA) secreted in human milk blocking the action of antigens on the intestinal mucosa.

Efamol Limited has developed pharmaceutical and dietetic compositions containing linoleic acid metabolites (including dihomo-γ-linolenic acid) for use in the treatment of manifest atopy. For example, Horrobin in U.S. Pat. No. 4,681,896, issued Jul. 21, 1987, teaches a method for treating atopic disorders. In this treatment, one or more metabolites of linoleic acid and one or more metabolites of α-linolenic acid are administered as such, or in the form of an ester, salt, amide or other derivative convertible in the body thereto alone or in an acceptable pharmaceutical carrier or diluent. (This patent is herein incorporated by reference.) As clearly evidenced in this patent, the role of desaturase enzymes, such as Δ-6-desaturase, was thought to be the critical component in the treatment of atopic dermatitis.

It is recognized that a Δ-6-desaturase deficiency or a deficient supply of linoleic acid metabolites is a cause for the subsequently occurring clinical manifestation of atopy, for reasons unrelated to the subject method of prophylaxis. In the case of Δ-6-desaturase deficiency, linoleic acid cannot be normally metabolized.

The subject invention focuses on the appropriate maturation and early differentiation of atopic lymphocytes in the thymus, the primary organ of the immune system. This has nothing in common with the correction or manipulation of functional disturbances of already inappropriately differentiated atopic T cells during manifest atopic disease as described by Horrobin.

DE-A-34 03 251 relates to a pharmaceutical dietetic composition for use in the treatment of atopic disorders wherein effective amounts of one or more metabolite(s) of linoleic acid and one or more metabolites of the α-linolenic acid are contained. Upon administration of γ-linolenic acid in the form of Evening Primrose Oil, biochemical deficits in manifest atopy are in part compensated for, and clinical improvements are provided.

From Chemical Abstracts, 98: 69 996v, it is known that γ-linolenic acid in the form of Evening Primrose Oil (Efamol) is capable of partially correcting the biochemical anomalies and the clinical status in manifest atopic dermatitis.

Traitler, et al. in U.S. Pat. No. 4,703,060, issued Oct. 27, 1987, describe a nutritive composition containing fatty substances and a process for their preparation. However, no mention is made of the use of these compositions in treating, much less preventing atopy.

From Chemical Abstracts, 100: 80453w, it is known that the increased capillary permeability in skin by intravenous injection of chemical mediators such as histamine, serotonin and bradykinin, is suppressed by the subcutaneous injection of prostaglandin $E_1$ ($PGE_1$). Investigations carried out with rats demonstrated an in vivo effect of prostaglandins on the capillary permeability in immediate type allergic reactions.

Chemical Abstracts, 109: 209935x, relates to a food composition containing omega(ω)-6-unsaturated fatty acids which are alleged to serve in the prevention and treatment of atopic dermatitis, in addition to other purposes. More particularly, a jelly containing only 3% γ-linolenic acid oil (corresponding to 8% of γ-linolenic acid in the oil) is stated as preventing "hangover". The prevention of atopic dermatitis, however, is the treatment of persons already suffering from manifest atopic disease as described by Horrobin.

EP-A-0 292 403 relates to prostaglandin-lipid formulations which may be used for the treatment of, among other things, bronchial asthma.

Because of ethical considerations, appropriate maturation and early differentiation of atopic lymphocytes in the human thymus could not be evaluated. However, since filing the parent patent application, the subject method of preventing atopy has received widespread approval of leaders in the fields of dermatology and medicine. Moreover, a recent paper (B. Dvorak and R. Stepankova, "Prostaglandins Leukotrienes and Essential Fatty Acids", 40:183–190 (1992), herein incorporated by reference) has reported that "the period immediately following birth, characterized by rapid development of neuroendocrine regulation in very young rats, crucially affects not only the physiological development of the organism but also development of the immune system. A nutritional deficiency of essential fatty acids in this period inflicts serious damage on the function of thymus, imposing a long-term effect on the cell-mediated immune response." Thus, in vivo support now exists for the subject method.

No method for atopy prophylaxis and prevention has ever previously been described.

Known treatments of atopy have generally used substances such as antihistamines, glucocorticoids and betasympatheticomimetic agents. In practice there has long been a great need for fast-acting substances which, especially in the case of an acute manifest atopy in the dermal and mucosal regions, will provide immediate relief.

The subject invention further provides a new use for $PGE_1$, $PGE_1$ derivatives and $PGE_1$ analogs, their physiologically compatible salts, esters, amides, phospholipids and glycolipids thereof as well as their precursors for the topical and inhalative treatments of acute manifest atopies in the dermal and mucosal areas.

Japanese Laid-Open Patent Application [JP-OS] 88/145230 (63/145230) relates to the use of prostaglandin $E_1$ as a therapeutic and prophylactic pharmaceutical for the treatment of certain brain diseases. It is also known from the JP-OS 87/223120 (62/223120) that AIDS may possibly be controlled by a combination treatment with various prostaglandins.

According to the EP-OS 257 859, a combination tissue plasminogen activator-prostaglandin can be used as a thrombolytic agent. EP-OS 100 630 relates to analogs of $PGE_1$ which can be employed for protection against cytotoxic substances, above all in the liver. From the German Laid-Open Patent Application DE-OS 33 15 356 it is known that $PGE_1$ derivatives and their cyclodextrin inclusion complexes as well as their salts can be employed, when administered orally or parenterally, against brain ischemia. Various other literature references relate to the synthesis and use of $PGE_1$ derivatives and analogs.

No above-mentioned reference anticipates, teaches or suggests the use of prostaglandin $E_1$, its derivatives, analogs and precursors for the treatment of forms of acute manifest atopy in the dermal and mucosal areas.

SUMMARY OF THE INVENTION

The subject invention provides a method for atopy prophylaxis which comprises administering to a preimmunocompetent human an atopy prophylactic amount of at least one substance selected from the group consisting of $\gamma$-linolenic acid, dihomo-$\gamma$-linolenic acid, prostaglandin $E_1$.

The subject method may be augmented by further administering a thymus hormone or prostaglandin $E_2$. As used herein, the terms prostaglandin $E_1$ ($PGE_1$) and prostaglandin $E_2$ ($PGE_2$) are to include physiologically acceptable analogs and derivatives having similar physiological activities. Likewise, the terms $PGE_1$, $PGE_2$, $\gamma$-linolenic acid and dihomo-$\gamma$-linolenic acid are to include physiologically compatible salts, esters, amides, phospholipids, glycolipids, etc., and may be administered as such.

This method may be accomplished in one of three manners, i.e., to a newborn, via breast feeding or in utero.

For the newborn, administration is parenterally or orally. Gamma-linolenic acid, dihomo-$\gamma$-linolenic acid or the combination thereof, is preferably administered in an amount of from about 10 to about 4,000 mg/day, and more preferably from about 100 to about 400 mg/day. When prostaglandin $E_1$ is administered, a daily intake of from about 0.01 to about 200 µg/day is preferred, and from about 0.1 to about 20 µg/day is more preferred.

For newborns, administration is typically via an infant formula. The infant formula preferably contains from about 1 to about 1,500 mg, and more preferably from about 10 to about 150 mg of $\gamma$-linolenic acid, dihomo-$\gamma$-linolenic acid, or combination thereof, per 100 ml of formula.

An infant formula with $PGE_1$, $PGE_2$, or combinations thereof, preferably contains from about 0.001 to about 20.0 µg of prostaglandin $E_1$ or $E_2$ per 100 ml of formula, and more preferably from 0.01 to about 2.0 µg of prostaglandin $E_1$ or $E_2$ per 100 ml of formula.

For administration via breast feeding, the subject method comprises introducing an amount of substance selected from the group consisting of $\gamma$-linolenic acid, dihomo-$\gamma$-linolenic acid and combinations thereof, into a nursing woman in an amount sufficient to cause the expression of a physiologically effective amount of a substance selected from the group consisting of $\gamma$-linolenic acid, dihomo-$\gamma$-linolenic acid, $PGE_1$ and combinations thereof, in the woman's milk. The breast milk containing an atopy prophylactic amount of the substance is then administered, either directly or indirectly, to a preimmuno-competent human. The nursing woman is given $\gamma$-linolenic acid, dihomo-$\gamma$-linolenic acid or combinations thereof, so that her preferred daily intake is from about 15 to about 15,000 mg/day, and more preferably from about 150 to about 1,500 mg/day.

For administration to a fetus in utero, the method comprises introducing an amount of a substance selected from the group consisting of $\gamma$-linolenic acid, dihomo-$\gamma$-linolenic acid and combinations thereof, into a pregnant woman in an amount sufficient to cause the expression of an atopy prophylactic amount of a substance selected from the group of $\gamma$-linolenic acid, dihomo-$\gamma$-linolenic acid, $PGE_1$ and combinations thereof, to the woman's fetus. For the administration of $\gamma$-linolenic acid, dihomo-$\gamma$-linolenic acid or combinations thereof, the preferable intake to the pregnant woman is from about 10 to about 10,000 mg/day, and more preferably from about 100 to about 1,000 mg/day.

DETAILED DESCRIPTION OF THE INVENTION

The subject invention is predicated on a new understanding of atopy unknown to the prior art. Atopy patients suffer from a lack of gamma ($\gamma$)-linolenic acid and the metabolites thereof, which was presumed attributable to a defect in delta ($\Delta$)-6-desaturase. In clinical atopy patients, this enzyme can no longer ensure sufficient reaction of linoleic acid to $\gamma$-linolenic acid. Based on this understanding, it is known that administration of $\gamma$-linolenic acid, e.g. in the form of Evening Primrose oil, compensates for this biochemical defect and alleviates atopic symptoms. The administered $\gamma$-linolenic acid cannot be produced in sufficient amounts by the deficient $\Delta$-6-desaturase. Thus, the prior art teaches that a defect in $\Delta$-6-desaturase (as well as its consequence, acute atopy) can be treated by administering $\gamma$-linolenic acid and its intermediate metabolites dihomo-$\gamma$-linolenic acid and arachidonic acid.

Inasmuch as atopy prophylaxis is referred to at all in the prior art, it is understood to mean preventing the above-mentioned biochemical defect, i.e., compensating for a deficiency of $\Delta$-6-desaturase from the beginning of human life. Known atopy prophylaxis is merely aimed at preventing acute manifest forms of atopy. The thoroughgoing prophylaxis of the present invention has never been foreseen.

The present invention provides a method of primary atopy prophylaxis. The term "prophylaxis" as used herein means a primary prevention resulting in the elimination or substantial minimization of factors injurious to health before these factors manifest themselves.

This method is attained in a surprisingly simple way by administering an agent containing at least one substance selected from the group consisting of $\gamma$-linolenic acid (GLA), dihomo-$\gamma$-linolenic acid (DGLA), the physiologically compatible salts, esters, amides, phospholipids, glycolipids thereof, and prostaglandin $E_1$ ($PGE_1$), $PGE_1$ derivatives or $PGE_1$ analogs, to a preimmunocompetent human (pre- or post-natal). Also useful are the following combinations of compounds:

—GLA + DGLA
—GLA + $PGE_1$
—DGLA + $PGE_1$
—GLA + DGLA + $PGE_1$

—GLA + $PGE_2$
—DGLA + $PGE_2$
—GLA + DGLA + $PGE_2$

—GLA + $PGE_1$ + $PGE_2$
—DGLA + $PGE_1$ + $PGE_2$
—GLA + DGLA + $PGE_1$ + $PGE_2$

For an infant, these substances should preferably be included in their food and/or administered concurrently. Gamma-linolenic acid occurs in the oil of the Evening Primrose (*Oenothera biennis*) and in the seeds of black currants (*Ribes nigrum*). There are also a number of other natural sources of γ-linolenic acid (e.g. *Borago officinalis*). Dihomo-γ-linolenic acid is obtainable by the process according to EP-A-252 716 from cultures of Mortierella, among other sources.

Important metabolites of linolenic acid include, among others, γ-linolenic acid and dihomo-γ-linolenic acid. In vivo, dihomo-γ-linolenic acid is metabolized to form $PGE_1$, among other products. $PGE_1$ is recognized by the subject invention as the essential mediator (stimulus), together with thymic hormones such as thymopoietin, thymulin and thymostimulin, for normal conditioning and maturing of the immune system of the newborn and young baby. The defect in maturation and differentiation of the immune system in an atopic person results in an excessive/uncontrolled formation of IgE in the manifest stage, i.e., serum IgE levels increase after contact with an allergen. Prophylaxis of atopy should start prebirth or immediately after birth, at a time when clinical manifestation usually is not yet observed and the conditioning and thorough maturation of the cellular immune system is not yet complete.

The agent for atopy prophylaxis used in the subject invention is typically in the form of a baby food (e.g., mother's milk or commercial preparations) containing at least one substance selected from the group consisting of γ-linolenic acid, dihomo-γ-linolenic acid, the physiologically compatible salts, esters, amides, phospholipids, glycolipids thereof, and $PGE_1$, $PGE_1$ derivatives and $PGE_1$ analogs.

The term "baby foods" includes, but is not limited to, foodstuffs of powderized, pulpy, dried or liquid consistency, including, among others, certified milk, evaporated milk, partially adapted and fully adapted finished food, high-protein low-fat finished food, milk-free finished food, hypoallergenic finished food, goat's milk preparations and mother's milk.

The substances in the agent are preferably contained in liposomes formed from phospho- and/or glycolipids. Preferred are liposomes formed from phospho- and/or glycolipids of the γ-linolenic acid and/or dihomo-γ-linolenic acid, and a particularly preferred agent contains $PGE_1$, its derivatives and/or analogs in liposomes, together with an antioxidant.

In a preferred embodiment of the process according to the invention, γ-linolenic acid, dihomo-γ-linolenic acid, the physiologically compatible salts, esters, amides, phospholipids, and glycolipids thereof are provided in a concentration sufficient to ensure a daily dose shown in Table 1 (ranges are approximate).

TABLE 1

| | Preferred amounts of substances Newborn infants/infants, 0–1 yr | |
|---|---|---|
| Substance | Daily Intake | Amount in infant formula |
| GLA | 100–400 mg/day | 10–150 mg/100 ml |
| DGLA | 100–400 mg/day | 10–150 mg/100 ml |
| GLA + DGLA | 50–200 mg/day | 5–75 mg/100 ml |
| | 50–200 mg/day | 5–75 mg/100 ml |
| $PGE_1$ | 0.1–20 µg/day | 0.01–2.0 µg/100 ml |
| $PGE_2$ | 0.1–20 µg/day | 0.01–2.0 µg/100 ml |
| $PGE_1$ + $PGE_2$ | 0.05–10 µg/day | 0.005–1.0 µg/100 ml |
| | 0.05–10 µg/day | 0.005–1.0 µg/100 ml |

These substances or combinations thereof are orally administered to the infant as pure or modified or concentrated plant oils (borage oil or evening primrose oil) or concentrates of GLA or DGLA-producing algae (e.g., Spirulina) or fungi (e.g., *Mucor ambiguous, Mortierella ramanniana*). These compounds are stored in light-protected gelatine capsules or ampules with the appropriate antioxidants (vitamin E or C, each 10 mg per 500 mg oil). The oils may be injected into the infant's mouth during nursing or breast feeding or may be added to a baby bottle immediately before feeding.

The substances or combinations thereof may also be incorporated into different types of infant formula, preferably into hypoallergenic infant formula. Table 4 gives a representative example of such an infant formula. Additionally, the substances might be incorporated into dried or lyophilized powder for the preparation of infant formula, or may be incorporated into baby pap, vegetable mash, pastes, or other preserved baby food products.

The amounts of substances to be administered to a pregnant woman are listed in Table 2. Prostaglandins would not be administered since they are known to induce labor.

TABLE 2

| | Pregnant Women |
|---|---|
| Substance | Daily oral uptake during pregnancy |
| GLA | 100–1000 mg/day |
| DGLA | 100–1000 mg/day |
| GLA + DGLA | 50–500 mg/day |
| | 50–500 mg/day |

Table 3 shows the ranges of substances to be administered to nursing mothers to ensure sufficient expression of the selected substances in the breast milk.

TABLE 3

| | Nursing atopic mother |
|---|---|
| Substance | Daily oral uptake during lactation |
| GLA | 150–1500 mg/day |
| DGLA | 150–1500 mg/day |
| GLA | 75–750 mg/day |
| + DGLA | 75–750 mg/day |

Table 4 shows appropriate nutrient composition of a proposed formula for feeding atopic and "atopy-at-risk" infants

TABLE 4

| Compound | Amounts per 100 ml |
|---|---|
| *γ-linolenic acid (GLA) from EPO | 150 mg |
| *Dihomo-γ-linolenic acid (DGLA) | 50 mg |
| *Prostaglandin $E_1$ ($PGE_1$) | 1.3 µg |
| *Prostaglandin $E_2$ ($PGE_2$) | 0.5 µg |
| Evening primrose seed oil (EPO) | 1.5 g |
| cis-Linoleic acid | 1.0 g |
| Medium chain triglycerides | 4.6 g |
| Soy bean protein | 1.9 g |
| Carbohydrates (40% maltodextrin, 40% lactose, 20% glucose) | 8.2 g |
| Potassium | 65 mg |
| Sodium | 45 mg |
| Calcium | 40 mg |
| Magnesium | 7.0 mg |
| Phosphorous | 26 mg |
| Chloride | 58 mg |
| *Zinc | 0.55 mg |
| Iron | 0.75 mg |
| Copper | 0.06 mg |
| Iodine | 9.0 µg |
| Fluoride | 0.05 mg |
| Manganese | 0.11 µg |
| Selenium | 0.01 µg |
| Vitamin A | 0.035 mg |
| Vitamin $D_3$ | 0.65 µg |
| Vitamin E | 0.60 mg |
| Vitamin $K_1$ | 1.5 µg |
| Vitamin $B_1$ | 0.035 mg |
| Vitamin $B_2$ | 0.063 mg |
| vitamin $B_6$ | 0.05 mg |
| Vitamin $B_{12}$ | 0.15 µg |
| *Ascorbyl palmitate (preservative, antioxidant) | 100 mg |
| Calcium pantothenate | 0.35 mg |
| Folic acid | 5.5 µg |
| Biotin | 6.4 µg |
| Niacinamide | 0.55 mg |
| Choline | 8.0 mg |
| Inositol | 5.0 mg |

*Primary prophylactic substance.

The agents according to the invention may also contain linoleic acid. Furthermore, an antioxidant, preferably vitamin E, vitamin C and/or derivatives thereof, may be present. As a further additive, prostaglandin $E_2$ ($PGE_2$) can be present. In a further preferred embodiment of the invention, the agent according to the invention contains $Ca^{2+}$, $Zn^{2+}$ and/or $Fe^{2+}$ ions. It is preferred that about 100 g of the agent according to the invention contain:

a) from about 10 to 40 mg of γ-linolenic acid and/or dihomo-γ-linolenic acid;

b) from about 0.15 to about 0.7 mg of a physiologically compatible zinc salt;

c) from about 5 to about 10 mg of ascorbic acid; and d) about 0.7 mg of α-tocopherol.

In a further preferred embodiment of the subject invention, the agent contains a thymus hormone, such as thymopoietin, thymulin, thymostimulin or thymopoietin acetate. Since thymus hormones might be destroyed in the stomach by oral administration, it is preferred that the thymus hormones are injected subcutaneously after administration of γ-linolenic acid, dihomo-γ-linolenic acid, $PGE_1$ and/or $PGE_2$.

The present invention further provides a process for preparing an agent for atopy prophylaxis, wherein at least one substance selected from the group consisting of γ-linolenic acid, dihomo-γ-linolenic acid, the physiologically compatible salts, esters, amides, phospholipids, glycolipids thereof, and $PGE_1$, $PGE_1$ derivatives and $PGE_1$ analogs, is added to a baby food. The substances are preferably dried, spray-dried or lyophilized. Such drying may be enhanced by the addition of albumin, such as hen's egg albumin.

A further subject matter of the present invention is the use of γ-linolenic acid, dihomo-γ-linolenic acid, the physiologically compatible salts, esters, amides, phospholipids, glycolipids thereof, and $PGE_1$, $PGE_1$ derivatives and $PGE_1$ analogs for atopy prophylaxis, wherefor these substances do not necessarily have to be present in combination with a baby food. The invention preferably comprises other enteral, parenteral or topical forms of application. In a particularly preferred manner, suppositories or oily solutions can be used for this purpose. The use according to the invention may also be contemplated for breast-feeding atopic mothers.

It is preferred that the use according to the invention provides the following daily doses:

a) from about 100 to about 400 mg of γ-linolenic acid and/or dihomo-γ-linolenic acid;

b) from about 1.5 to about 7.0 mg of a physiologically compatible zinc salt;

c) from about 38 to about 113 mg of ascorbic acid; and d) from about 3.5 to about 11 mg of α-tocopherol.

The subject invention may contain a thymus hormone preferably provided at a daily dose of from about 0.2 to about 2 mg/kg of body weight. Thymus hormone or thymus hormone active peptide, (e.g. thymopentin (TP-5)) may be administered to the baby either simultaneously or at a different time or by a different means of administration (e.g. subcutaneous injection). In a further preferred embodiment, the substances are parenterally and/or orally administered to the baby.

In a critical phase of the post-partum maturing of the immune system, the inventors realized that by administering the subject agents, a baby is supplied with sufficient amounts of those substances which are determining factors in the formation and maturation of a well-balanced functional immune system. More specifically, the administration of γ-linolenic acid and/or its metabolites and the $PGE_1$ derivatives and/or analogs together with thymus hormones results in the desired effect.

Another object of the present invention is to provide an immediately effective agent in cases of acute manifest atopies in the dermal and mucosal areas. This may be attained through the use of $PGE_1$, its derivatives and analogs for the treatment of atopy.

One or more compound(s) of the group consisting of $PGE_1$, $PGE_1$ derivatives and $PGE_1$ analogs, their physiologically compatible salts, esters, amides, phospholipids and glycolipids may be employed for the treatment of acute manifest atopies in the dermal and mucosal areas. The process of using these agents encompasses administration in physiologically effective and compatible amounts of the substances of the invention for topical or inhalative application in the form of eye drops, nose sprays, creams, lotions or also in the form of aerosols. It is preferred that at least one substance selected from the group consisting of γ-linolenic acid, 15-hydroxy-dihomo-γ-linolenic acid and dihomo-γ-linolenic acid, the physiologically compatible salts, esters, amides, phospholipids and glycolipids thereof is added to the substances according to the invention.

An advantage of the present invention is to provide $PGE_1$ therapy offering immediate relief from the atopic symptoms. Furthermore, the use of the substances according to the invention in combination with γ-linolenic acid and/or dihomo-γ-linolenic acids and/or the pharmacologically reasonable dosage forms thereof may contribute to some prevention, since these substances, as a rule, are only slowly metabolized to form $PGE_1$.

The above-described embodiments are illustrative of the application of the principles of the invention. Numerous other arrangements, processes, methods, compositions, uses, or agents may be devised by those skilled in the art without departing from the spirit and scope of the invention. Accordingly, the subject application is only to be limited by the claims that follow and their equivalents.

What is claimed is:

1. A method for atopy prophylaxis which comprises orally administering an atopy-prophylactic effective amount of an atopy-prophylaxis dietary supplement to a human child at a time before atopy is clinically manifest in the child and before conditioning and thorough maturation of a cellular immune system of the child is complete, the atopy-prophylaxis dietary supplement comprising at least one substance selected from the group consisting of γ-linolenic acid; and dihomo-γ-linolenic acid.

2. The method of claim 1 in which the atopy-prophylaxis dietary supplement comprises γ-linolenic acid, the γ-linolenic acid being administered in an amount of from about 10 to about 4,000 mg/day.

3. The method of claim 2 in which the γ-linolenic acid is administered in an amount of from about 100 to about 400 mg/day.

4. The method of claim 1 in which the atopy-prophylaxis dietary supplement comprises the dihomo-γ-linolenic acid, the dihomo-γ-linolenic acid being administered in an amount of from about 10 to about 4,000 mg/day.

5. The method of claim 4 in which the dihomo-γ-linolenic acid is administered in an amount of from about 100 to about 400 mg/day.

6. The method of claim 1, further comprising administering an atopy-prophylactic effective amount of a thymus hormone.

7. The method of claim 6 in which the thymus hormone is selected from the group consisting of thymopoietin, thymulin, thymostimulin, thymopoietin acetate, and thymopentin (TP-5).

8. The method of claim 6 in which the thymus hormone or thymus-hormone active peptide is administered in an amount of from about 0.2 to about 2 mg/day per kilogram of body weight of the child.

9. The method of claim 1 in which the atopy-prophylaxis dietary supplement is administered in an infant formula.

10. The method of claim 9 in which the infant formula contains from about 1 to about 1,500 mg of γ-linolenic acid per 100 ml of formula.

11. The method of claim 10 in which the infant formula contains from about 10 to about 150 mg of γ-linolenic acid per 100 ml of formula.

12. The method of claim 9 in which the infant formula contains from about 1 to about 1,500 mg of dihomo-γ-linolenic acid per 100 ml of formula.

13. The method of claim 12 in which the infant formula contains from about 10 to about 150 mg of dihomo-γ-linolenic acid per 100 ml of formula.

14. The method of claim 1 in which the child is a newborn.

* * * * *